United States Patent
Ouchi

(10) Patent No.: US 6,224,611 B1
(45) Date of Patent: May 1, 2001

(54) SNARE FOR ENDOSCOPE

(75) Inventor: Teruo Ouchi, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/386,485

(22) Filed: Aug. 31, 1999

(30) Foreign Application Priority Data

Sep. 14, 1998 (JP) .................................. 10-259775

(51) Int. Cl.$^7$ .................................. A61B 17/24
(52) U.S. Cl. .................................. 606/113
(58) Field of Search .................................. 606/113, 79

(56) References Cited

U.S. PATENT DOCUMENTS

| | | |
|---|---|---|
| 4,643,187 | 2/1987 | Okada . |
| 5,330,482 * | 7/1994 | Gibbs et al. .................. 606/113 |
| 5,376,094 * | 12/1994 | Kline .................. 606/113 |
| 5,496,330 * | 3/1996 | Bates et al. .................. 606/113 |
| 5,957,932 * | 9/1999 | Bates et al. .................. 606/113 |
| 6,013,086 * | 1/2000 | Ouchi et al. .................. 606/113 |

FOREIGN PATENT DOCUMENTS

| | | |
|---|---|---|
| 5176941 | 11/1981 | (JP) . |
| 56-160516 | 11/1981 | (JP) . |
| 4-146743 | 5/1992 | (JP) . |
| 8-224254 * | 8/1996 | (JP) .................. 606/113 |

* cited by examiner

Primary Examiner—John J. Wilson
Assistant Examiner—Eduardo C. Robert
(74) Attorney, Agent, or Firm—Greenblum & Bernstein P.L.C.

(57) ABSTRACT

A snare for an endoscope includes a control wire axially movably inserted in a flexible sheath. A snare loop formed by an elastic wire is connected to the distal end of the control wire. When the control wire is advanced, the snare loop projects from the distal end of the sheath and expands in a loop shape by its own elasticity. When the control wire is retracted, the snare loop is pulled into the sheath and folded. The snare loop is formed by two elastic wires between two mutually secured portions of the elastic wires, which are laid in parallel and in close contact with each other and secured together directly at two longitudinally spaced positions. The control wire is formed by an extending portion of at least one of the elastic wires that extends rearward from the mutually secured portion at the rear end of the snare loop.

18 Claims, 5 Drawing Sheets

SNARE FOR ENDOSCOPE

BACKGROUND OF THE INVENTION

The present disclosure relates to subject matter contained in Japanese Patent Application No. 10-259775 (filed on Sep. 14, 1998), which is expressly incorporated herein by reference in its entirety.

1. Field of the Invention

The present invention relates to a snare that is inserted into an instrument-inserting channel of an endoscope to excise a polyp.

2. Description of the Prior Art

FIG. 5 shows a distal end portion of a conventional snare for use with an endoscope. In a flexible sheath 1, a control wire 2 is axially movably inserted, and a snare loop 3 formed by an elastic wire is connected to the distal end of the control wire 2 through a connecting pipe 4.

At the distal end of the snare loop 3, a single elastic wire is bent back in a U-shape as shown in FIG. 5. Alternatively, two elastic wires are inserted into a binding pipe (not shown) so as to be secured together therein.

By virtue of the above-described arrangement, the snare loop 3 projects from or withdraws into the distal end of the flexible sheath 1 in response to an operation of advancing or retracting the control wire 2 in the axial direction. When projecting from the distal end of the flexible sheath 1, the snare loop 3 expands in a loop shape by its own elasticity. When pulled into the distal end of the flexible sheath 1, the snare loop 3 is folded.

To excise a polyp with the snare, the base of the polyp is encircled with the snare loop 3 expanded by being pushed out from the distal end of the flexible sheath 1. In this state, the control wire 2 is pulled toward the proximal end of the flexible sheath 1 (rightward as viewed in FIG. 5).

Consequently, the snare loop 3 is gradually pulled into the flexible sheath 1 while reducing the loop size, causing the polyp to be pinched tight with the snare loop 3. If a high-frequency electric current is supplied to the snare loop 3 through the control wire 2 in this state, the polyp is cut off without bleeding.

In the conventional snare for an endoscope having the above-described structure, however, the inner diameter d of the flexible sheath 1 must be larger than the outer diameter of the connecting pipe 4, which connects together the control wire 2 and the two portions of the single elastic wire or the two elastic wires that constitute the snare loop 3. In a case where the width W of the distal end portion of the snare loop 3 is larger than the outer diameter of the connecting pipe 4, the inner diameter d of the flexible sheath 1 must be larger than the width W.

Consequently, the inner diameter of the flexible sheath 1 becomes considerably large. Therefore, when the control wire 2 is pulled to pinch a polyp tight with the snare loop 3, the polyp may be undesirably drawn into the flexible sheath 1. This may hinder the polyp excision treatment.

SUMMARY OF THE INVENTION

An object of the present invention is to provide a snare for an endoscope that is designed so that a polyp pinched tight with the snare loop is unlikely to be drawn into the flexible sheath, and thus a polyp excision treatment can be performed safely and smoothly.

Other objects and advantages of the present invention will become apparent from the following detailed description of illustrated embodiments of the invention.

According to the present invention, there is provided a snare for an endoscope including a control wire axially movably inserted in a flexible sheath. A snare loop is formed by an elastic wire and connected to the distal end of the control wire. When the control wire is advanced axially, the snare loop projects from the distal end of the flexible sheath and expands in a loop shape by its own elasticity. When the control wire is retracted axially, the snare loop is pulled into the distal end of the flexible sheath and folded. The snare loop is formed by two elastic wires between two mutually secured portions of the elastic wires, which are laid in parallel and in close contact with each other and secured together directly at two positions longitudinally spaced apart from each other. The control wire is formed by an extending portion of at least one of the two elastic wires that extends rearward from one of the two mutually secured portions that is at the rear end of the snare loop.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
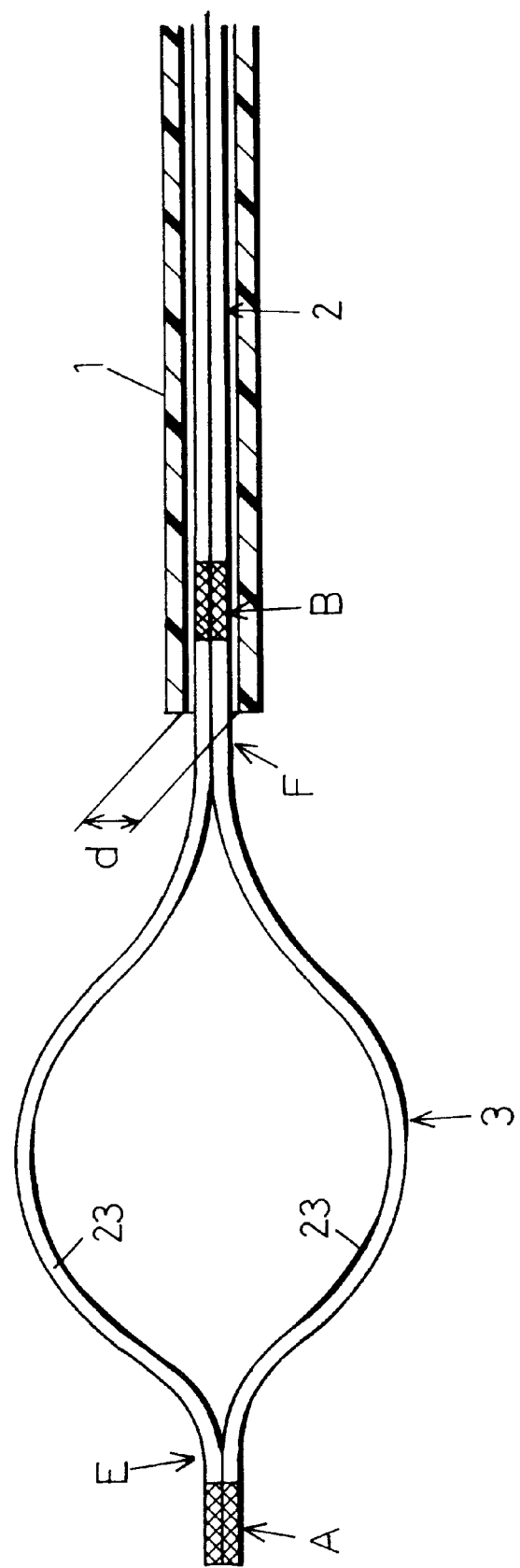
FIG. 1 is a sectional plan view of a distal end portion of a snare for an endoscope according to a first embodiment of the present invention.

FIG. 1 shows a distal end portion of a snare for an endoscope according to a first embodiment of the present invention. A flexible sheath 1 is formed from a tetrafluoroethylene resin tube, for example. The flexible sheath 1 is removably inserted into an instrument-inserting channel of an endoscope (not shown).

A snare loop 3 is formed by two electrically conductive elastic wires 23. Under conditions where no external force is applied thereto, the snare loop 3 forms a smoothly curved loop with a diameter of several centimeters. As each elastic wire 23, a single or stranded wire of stainless steel with a diameter of the order of from 0.2 mm to 0.5 mm is used by way of example.

The snare loop 3 can be folded by elastic deformation of the elastic wires 23 under application of external force. When the external force is removed, the snare loop 3 is returned to the original loop shape by the elasticity of the elastic wires 23.

Figure 2:
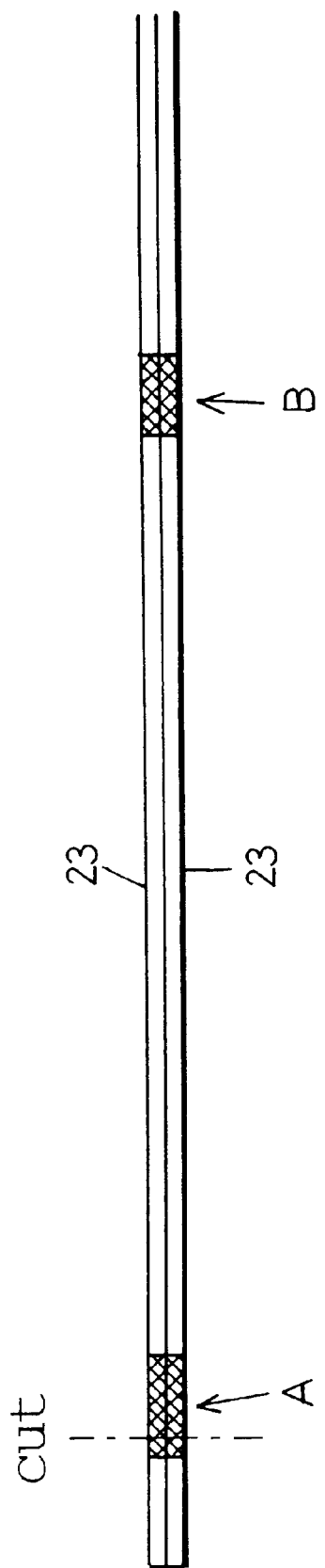
FIG. 2 is a plan view showing a step in the process of producing a snare loop in the first embodiment of the present invention.

The snare loop 3 is formed as follows. As shown in FIG. 2 by way of example, two elastic wires 23 are laid in parallel and in close contact with each other and secured together directly at two positions A and B longitudinally spaced apart from each other by a distance of the order of 3 cm to 10 cm by silver-alloy brazing, laser beam welding or plasma arc welding in such a manner that the diameter of each of the mutually secured portions A and B will not be larger than the sum total of the diameters of the two elastic wires 23. A distal end portion of the pair of elastic wires 23 is cut off at an intermediate point in the front secured portion A. Then, a portion of the pair of elastic wires 23 between the two mutually secured portions A and B is formed into a loop shape.

In the formation of the snare loop 3, as shown in FIG. 1, appropriate straight portions E and F are formed between the front and rear secured portions A and B and the loop portion lying therebetween. The provision of the straight portions E and F makes it possible to ensure durability to repeated use or the like.

The two elastic wires 23 that form the snare loop 3 extend rearward (rightward as viewed in FIG. 1) straight from the rear secured portion B. The extending portions of elastic wires 23 form a control wire 2.

The control wire 2 is axially movably inserted in the flexible sheath 1. The control wire 2 is actuatable to advance or retract as desired at a control part 10 (see FIG. 3) connected to the proximal end of the flexible sheath 1.

Figure 3:
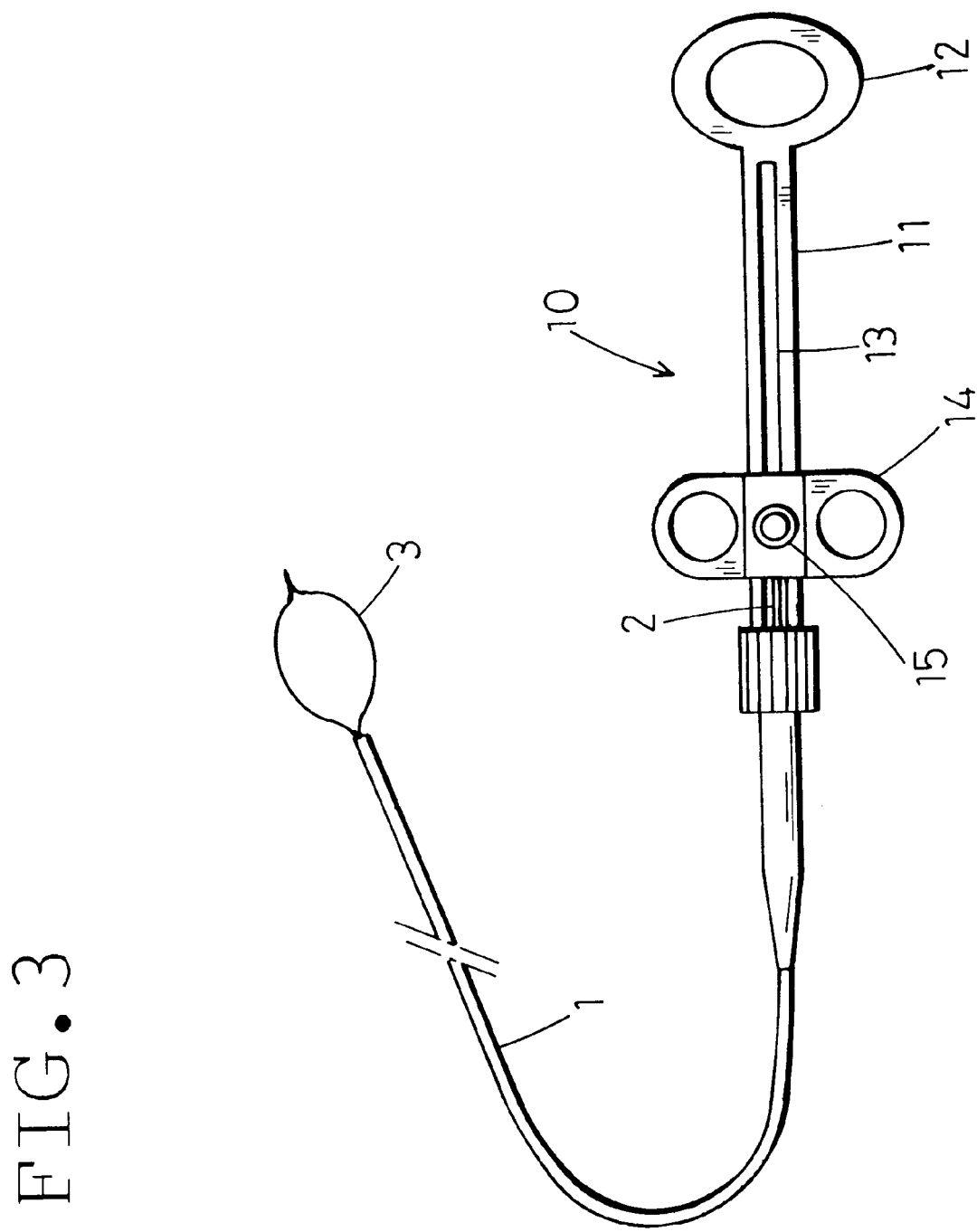
FIG. 3 is a plan view showing the whole arrangement of the snare according to the first embodiment of the present invention.

FIG. 3 shows the whole arrangement of the snare for an endoscope according to the first embodiment. The control part 10, which is connected to the proximal end of the flexible sheath 1, has an elongate control part body 11. A first finger engagement portion 12 is formed at the proximal end of the control part body 11. A second finger engagement portion is formed on a slider 14 that is slidable along a slit 13 formed in the longitudinal direction of the control part body 11.

The proximal end of the control wire 2 is firmly connected to the slider 14. Accordingly, as the slider 14 is advanced or retracted, the control wire 2 advances or retracts in the flexible sheath 1. Reference numeral 15 denotes a connecting terminal to which a high-frequency power supply cord (not shown) is connected. Thus, a high-frequency electric current can be supplied to the snare loop 3 through the control wire 2.

By virtue of the above-described arrangement, as the control wire 2 is actuated to advance or retract at the control part 10, the snare loop 3 projects from or withdraws into the distal end of the flexible sheath 1. When projecting from the distal end of the flexible sheath 1, the snare loop 3 expands in a loop shape by its own elasticity. When pulled into the distal end of the flexible sheath 1, the snare loop 3 is folded.

It is appropriate that the inner diameter d of the flexible sheath 1 should be larger than the maximum diameter of the control wire 2 by about 0.1 mm to 0.5 mm with a view to allowing the control wire 2, which is formed from two elastic wires 23, to move back and forth smoothly in the flexible sheath 1. Accordingly, the inner diameter d of the flexible sheath 1 is 1.5 mm at the maximum. That is, $d \leq 1.5$ mm.

Thus, in the present invention, the diameter of the joint B between the snare loop 3 and the control wire 2 is minimized, and the diameter of the distal end portion A of the snare loop 3 is the same as the diameter of the joint B. Therefore, the inner diameter d of the flexible sheath 1 can be reduced to a very small size.

To excise a polyp with the snare for an endoscope, the base of the polyp is encircled with the snare loop 3 expanded by being pushed out from the distal end of the flexible sheath 1. In this state, the control wire 2 is pulled toward the proximal end of the flexible sheath 1 (rightward as viewed in FIG. 1).

Consequently, the snare loop 3 is gradually pulled into the flexible sheath 1 while reducing the loop size, causing the polyp to be pinched tight with the snare loop 3. If a high-frequency electric current is supplied to the snare loop 3 through the control wire 2 in this state, the polyp is cut off without bleeding.

In the polyp excision treatment, the polyp will not be drawn into the flexible sheath 1 because in the snare for an endoscope according to the present invention the inner diameter of the flexible sheath 1 is very small, i.e. only 1.5 mm at the maximum. Therefore, the polyp excision treatment can be carried out safely and speedily.

Figure 4:
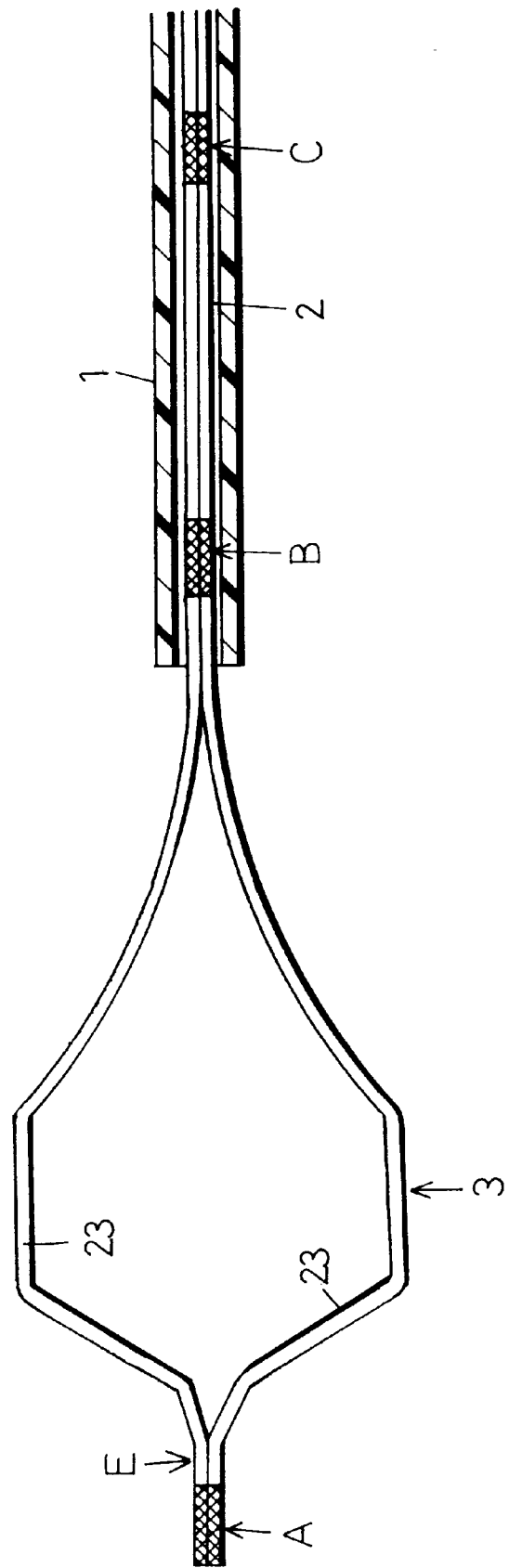
FIG. 4 is a sectional plan view of a distal end portion of a snare for an endoscope according to a second embodiment of the present invention.
Figure 5:
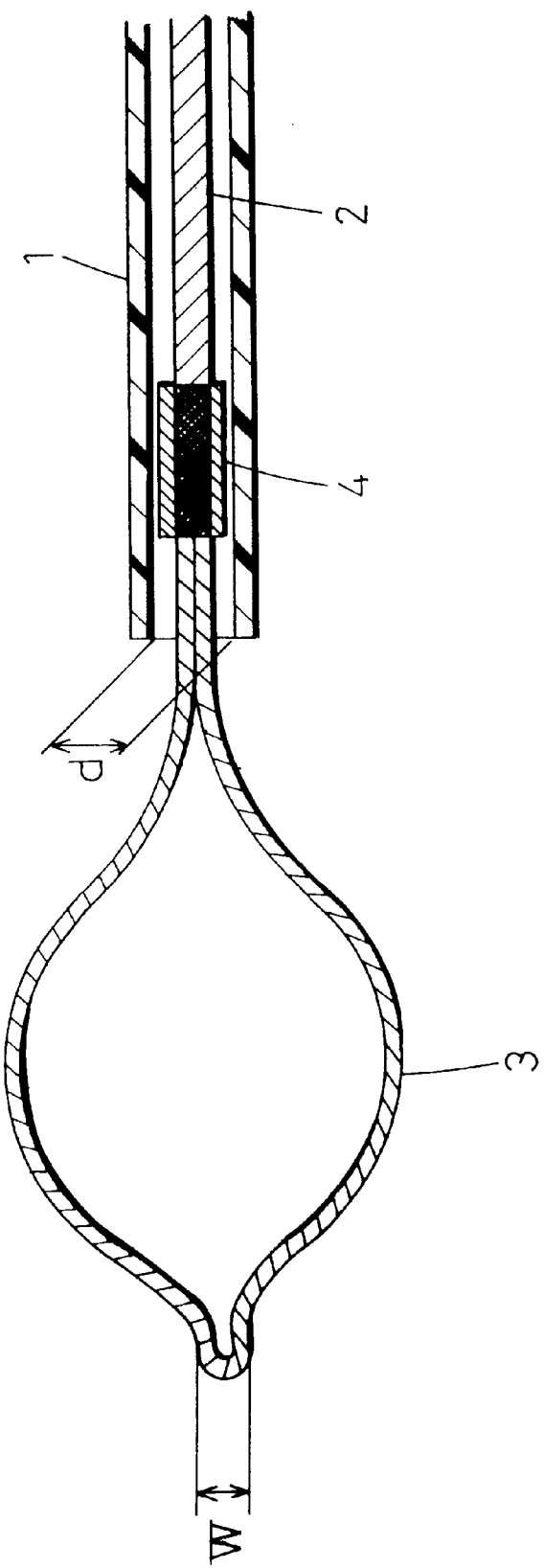
FIG. 5 is a sectional plan view of a distal end portion of a conventional snare for an endoscope.

It should be noted that the present invention is not necessarily limited to the above-described embodiment. As shown in FIG. 4 by way of example, the two elastic wires 23 may also be secured together directly in the state of axially extending in parallel and in close contact with each other at at least one intermediate portion C of the control wire 2.

The control wire 2 does not always need to be formed by two elastic wires 23 but may be formed by either of the elastic wires 23. The snare loop 3 may be formed in a polygonal shape, e.g. a hexagon or an octagon.

In addition, the present invention may also be applied to a basket type foreign body-recovering instrument for an endoscope in which at least three elastic wires project from or withdraw into a flexible sheath to expand or contract by their own elasticity.

According to the present invention, the thickest portion of the snare that is pulled into the flexible sheath can be formed with a diameter not larger than the sum total of the diameters of the two elastic wires. Therefore, the inner diameter of the flexible sheath can be reduced. As a result, a polyp pinched tight with the snare loop is unlikely to be drawn into the flexible sheath. Thus, the polyp excision treatment can be carried out safely and smoothly.

While the invention has been described by reference to specific embodiments chosen for purposes of illustration, it should be apparent that numerous modifications could be made thereto by those skilled in the art without departing from the basic concept and scope of the invention.

What is claimed is:

1. A snare for an endoscope comprising an axially movable control wire extending within a flexible sheath and a snare loop, said snare loop connected to a distal end of said control wire, wherein when said control wire is axially advanced, said snare loop projects from a distal end of said flexible sheath and expands into a loop shape due to elasticity of said snare loop, whereas when said control wire is axially retracted, said snare loop retracts into the distal end of said flexible sheath and is folded into a closed shape;

said snare loop comprising two elastic wires extending between two mutually secured portions, said two elastic wires extending parallel to each other and at least partially in close contact with each other, said two elastic wires being secured directly together at two positions longitudinally spaced from each other, each of said two mutually secured portions having an outer diameter not larger than a total of the diameters of said two elastic wires; and said control wire comprising a portion of at least one of said two elastic wires that extends rearwardly from the one of said two mutually secured portions that is positioned at a rear end of said snare loop.

2. A snare for an endoscope according to claim 1, said two elastic wires being secured together at said two mutually secured portions by one of silver-alloy brazing, laser beam welding, and plasma arc welding.

3. The snare for an endoscope according to claim 1, said snare loop, when projecting from said distal end of said flexible sheath, having a shape of a polygon.

4. A snare for an endoscope according to claim 1, straight portions being formed between a loop portion of said snare loop and at least one of said two mutually secured portion, respectively.

5. A snare for an endoscope according to claim 1, wherein each of said two elastic wires extend rearward from the mutually secured portion at the rear end of said snare loop to form said control wire.

6. A snare for an endoscope according to claim 1, said two elastic wires also being secured together while axially extending in parallel and in close contact with each other at at least one intermediate portion of said control wire.

7. A snare for an endoscope according to claim 1, said elastic wires comprising electrically conductive wires, a high-frequency electric current being suppliable to said snare loop through said control wire.

8. A snare for an endoscope according to claim 1, wherein said two elastic wires are secured together at said two mutually secured portions by one of silver-alloy brazing, laser beam welding, and plasma arc welding.

9. A snare for an endoscope comprising an axially movable control wire extending within a flexible sheath and a snare loop, said snare loop connected to a distal end of said control wire, wherein when said control wire is axially advanced, said snare loop projects from a distal end of said flexible sheath and expands into a loop shape due to elasticity of said snare loop, whereas when said control wire is axially retracted, said snare loop retracts into the distal end of said flexible sheath and is folded into a closed shape;

said snare loop comprising two elastic wires extending between two mutually secured portions, said two elastic wires extending parallel to each other and at least partially in close contact with each other, said two elastic wires being secured together at two positions longitudinally spaced from each other, both said elastic wires extending rearwardly from the mutually secured portion at a rear end of said snare loop to form said control wire.

10. A snare for an endoscope according to claim 9, wherein each of said two mutually secured portions has an outer diameter not larger than a total of the diameters of said two elastic wires.

11. A snare for an endoscope according to claim 10, wherein said two elastic wires are secured together at said two mutually secured portions by one of silver-alloy brazing, laser beam welding, and plasma arc welding.

12. A snare for an endoscope according to claim 9, said elastic wires comprising electrically conductive wires, a high-frequency electric current being suppliable to said snare loop through said control wire.

13. The snare for an endoscope according to claim 9, said two elastic wires being secured directly to each other at said two positions longitudinally spaced from each other.

14. The snare for an endoscope according to claim 9, sid snare loop, when projecting from said distal end of said flexible sheath, having a shape of a polygon.

15. A snare for an endoscope comprising an axially movable control wire extending within a flexible sheath, and a snare loop, said snare loop connected to a distal end of said control wire, wherein when said control wire is axially advanced, said snare loop projects from a distal end of said flexible sheath and expands into a loop shape due to elasticity of said snare loop, whereas when said control wire is axially retracted, said snare loop retracts into the distal end of said flexible sheath and is folded into a closed shape;

said snare loop comprising two elastic wires extending between two mutually secured portions, said two elastic wires extending parallel to each other and at least partially in close contact with each other, said two elastic wires being secured together at two positions longitudinally spaced from each other, said two elastic wires also being secured together while extending axially in parallel and in close contact with each other at at least one intermediate portion of said control wire; and said control wire comprising a portion of at least one of said two elastic wires that extends rearwardly from the one of said two mutually secured portions that is positioned at a rear end of said snare loop.

16. A snare for an endoscope according to claim 15, said elastic wires comprising electrically conductive wires, a high-frequency electric current being suppliable to said snare loop through said control wire.

17. The snare for an endoscope according to claim 16, said two elastic wires being secured directly to each other at said two positions longitudinally spaced from each other.

18. The snare for an endoscope according to claim 16, said snare loop, when projecting from said distal end of said flexible sheath, having a shape of a polygon.

* * * * *